US011000337B2

(12) United States Patent
Cooper et al.

(10) Patent No.: US 11,000,337 B2
(45) Date of Patent: May 11, 2021

(54) SYSTEMS AND METHODS FOR PROXIMAL CONTROL OF A SURGICAL INSTRUMENT

(71) Applicant: INTUITIVE SURGICAL OPERATIONS, INC., Sunnyvale, CA (US)

(72) Inventors: Thomas Grosvenor Cooper, Menlo Park, CA (US); David Quentin Larkin, Menlo Park, CA (US); David Joseph Rosa, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/379,314

(22) Filed: Apr. 9, 2019

(65) Prior Publication Data
US 2019/0231462 A1    Aug. 1, 2019

Related U.S. Application Data

(63) Continuation of application No. 15/590,710, filed on May 9, 2017, now Pat. No. 10,299,872, which is a
(Continued)

(51) Int. Cl.
*A61B 34/35*    (2016.01)
*A61B 34/37*    (2016.01)
(Continued)

(52) U.S. Cl.
CPC .............. *A61B 34/35* (2016.02); *A61B 34/30* (2016.02); *A61B 34/37* (2016.02); *A61B 34/74* (2016.02);
(Continued)

(58) Field of Classification Search
None
See application file for complete search history.

(56) References Cited

U.S. PATENT DOCUMENTS

| 5,595,965 A | 1/1997 | Wiggins |
| 5,685,821 A | 11/1997 | Pike |

(Continued)

FOREIGN PATENT DOCUMENTS

| EP | 1570789 B1 | 5/2008 |
| JP | 2009273829 A | 11/2009 |

(Continued)

OTHER PUBLICATIONS

Extended European Search Report for Application No. 14751850.0, dated Jun. 29, 2016, 9 pages.

(Continued)

*Primary Examiner* — Said Bouziane
(74) *Attorney, Agent, or Firm* — Haynes and Boone, LLP

(57) ABSTRACT

An instrument chassis for a robotic surgical system comprises a bridge member, a first instrument guide member configured to receive a first surgical instrument, and a second instrument guide member configured to receive a second surgical instrument. Each of the first instrument guide member and the second instrument guide member is moveably coupled to the bridge member such that each of the first instrument guide member and the second instrument guide member is moveable in at least one degree of freedom relative to the bridge member. The instrument chassis further comprises a central instrument guide member coupled to the bridge member between the first instrument guide member and the second instrument guide member. The central instrument guide member is configured to receive a third surgical instrument. Each of the first instrument guide member and
(Continued)

the second instrument guide member is slidably movable relative to the bridge member.

20 Claims, 7 Drawing Sheets

Related U.S. Application Data continuation of application No. 14/181,110, filed on Feb. 14, 2014, now Pat. No. 9,662,176.

(60) Provisional application No. 61/765,482, filed on Feb. 15, 2013.

(51) Int. Cl.
*A61B 34/30* (2016.01)
*A61B 34/00* (2016.01)
*A61B 17/00* (2006.01)
*A61B 90/00* (2016.01)

(52) U.S. Cl.
CPC ....... *A61B 17/00234* (2013.01); *A61B 90/361* (2016.02); *A61B 2017/00327* (2013.01); *A61B 2017/00477* (2013.01); *A61B 2034/301* (2016.02)

(56) References Cited

U.S. PATENT DOCUMENTS

| | | | |
|---|---|---|---|
| 5,687,145 A | 11/1997 | Takashina et al. |
| 5,792,135 A | 8/1998 | Madhani et al. |
| 5,817,084 A | 10/1998 | Jensen et al. |
| 6,331,181 B1 | 12/2001 | Tierney et al. |
| 6,424,885 B1 | 7/2002 | Niemeyer et al. |
| 6,441,577 B2 | 8/2002 | Blumenkranz et al. |
| 6,491,701 B2 | 12/2002 | Tierney et al. |
| 6,522,906 B1 | 2/2003 | Salisbury, Jr. et al. |
| 6,645,196 B1 | 11/2003 | Nixon et al. |
| 6,817,974 B2 | 11/2004 | Cooper et al. |
| 7,833,156 B2 | 11/2010 | Williams et al. |
| 7,942,868 B2 | 5/2011 | Cooper et al. |
| 7,963,913 B2 | 6/2011 | Devengenzo et al. |
| 7,996,110 B2 | 8/2011 | Lipow et al. |
| 8,182,415 B2 | 5/2012 | Larkin et al. |
| 8,518,024 B2 | 8/2013 | Williams et al. |
| 8,919,348 B2 | 12/2014 | Williams et al. |
| 9,060,678 B2 | 6/2015 | Larkin et al. |
| 9,662,176 B2 | 5/2017 | Cooper et al. |
| 2005/0273086 A1 | 12/2005 | Green et al. |
| 2007/0005002 A1 | 1/2007 | Millman et al. |
| 2007/0016174 A1 | 1/2007 | Millman et al. |
| 2007/0137371 A1 | 6/2007 | Devengenzo et al. |
| 2007/0173977 A1 | 7/2007 | Schena |
| 2009/0036740 A1 | 2/2009 | Finlay et al. |
| 2009/0084216 A1 | 4/2009 | Schena et al. |
| 2009/0326318 A1 | 12/2009 | Tognaccini et al. |
| 2011/0071542 A1 | 3/2011 | Prisco et al. |
| 2011/0071544 A1 | 3/2011 | Steger et al. |
| 2011/0118545 A1* | 5/2011 | Williams ........... A61B 1/00052 600/104 |
| 2011/0213384 A1* | 9/2011 | Jeong .................... A61B 34/30 606/130 |
| 2011/0277580 A1 | 11/2011 | Cooper et al. |
| 2014/0107665 A1 | 4/2014 | Shellenberger et al. |
| 2017/0239009 A1 | 8/2017 | Cooper et al. |

FOREIGN PATENT DOCUMENTS

| | | |
|---|---|---|
| JP | 2010099403 A | 5/2010 |
| JP | 2011010961 A | 1/2011 |
| KR | 20100048789 A | 5/2010 |
| WO | WO-0033755 A1 | 6/2000 |
| WO | WO-2007114975 A2 | 10/2007 |
| WO | WO-2007146987 A2 | 12/2007 |
| WO | WO-2009123891 A1 | 10/2009 |
| WO | WO-2010151438 A1 | 12/2010 |
| WO | WO-2011002215 A2 | 1/2011 |
| WO | WO-2011060031 A1 | 5/2011 |
| WO | WO-2012020386 A1 | 2/2012 |

OTHER PUBLICATIONS

International Search Report and Written Opinion for Application No. PCT/US2014/016552, dated Jun. 3, 2014, 15 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR PROXIMAL CONTROL OF A SURGICAL INSTRUMENT

CROSS-REFERENCE TO RELATED APPLICATIONS

This application is a continuation application of U.S. patent application Ser. No. 15/590,710, filed May 9, 2017, which is a continuation application of U.S. patent application Ser. No. 14/181,110, filed on Feb. 14, 2014, which claims the benefit of U.S. Provisional Application No. 61/765,482 filed Feb. 15, 2013, all of which are incorporated by reference herein in their entirety.

FIELD

The present disclosure is directed to surgical systems and methods for use in minimally invasive robotically assisted surgery, and more particularly to systems and methods for moving a surgical instrument about a pivot located proximally of an anatomical entry point.

BACKGROUND

Minimally invasive medical techniques are intended to reduce the amount of extraneous tissue that is damaged during diagnostic or surgical procedures, thereby reducing patient recovery time, discomfort, and deleterious side effects. Minimally invasive robotic surgical or telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

In robotically-assisted telesurgery, the surgeon typically operates a master controller to control the motion of surgical instruments at the surgical site from a location that may be remote from the patient (e.g., across the operating room, in a different room, or a completely different building from the patient). The master controller usually includes one or more hand input devices, such as hand-held wrist gimbals, joysticks, exoskeletal gloves or the like, which are operatively coupled to the surgical instruments that are releasably coupled to a patient side surgical manipulator ("the slave"). The master controller controls the instrument's position, orientation, and articulation at the surgical site. The slave is an electro-mechanical assembly which includes one or more arms, joints, linkages, servo motors, etc. that are connected together to support and control the surgical instruments. In a surgical procedure, the surgical instruments (including an endoscope) may be introduced directly into an open surgical site, through a natural orifice, or through cannulas into a body cavity.

For minimally invasive surgical procedures, the surgical instruments, controlled by the surgical manipulator, may be introduced into the body cavity through a single surgical incision site, multiple closely spaced incision sites on the patient's body, and/or one or more natural orifices in the patient anatomy. For some minimally invasive surgical procedures performed through particularly small entry ports, multiple surgical instruments may be introduced in a closely gathered cluster with nearly parallel instrument shafts. Previous surgical systems and techniques maintained a common center of motion, known as a "remote center," at an area near the anatomical entry point. Attempts to maintain a center of rotation at the anatomical entry point, through a particularly narrow surgical incision or a particularly narrow natural orifice such as a human throat or cervix, may result in the collision of the proximal ends of the surgical instruments. Improved systems and methods are needed for controlling these surgical instruments while minimizing the occurrence of surgical instrument collisions.

SUMMARY

The embodiments of the invention are summarized by the claims that follow below.

In one embodiment, a robotic surgical system comprises an instrument chassis having a proximal mounting section and a distal mounting section. The system also comprises an instrument guide movably coupled to the distal mounting section and an actuator coupled to the proximal mounting section. A linkage system operably interconnects the actuator and the instrument guide to transmit motion from the actuator to the instrument guide.

In another embodiment, a robotic surgical method comprises providing an instrument chassis having a proximal mounting section and a distal mounting section. An instrument guide assembly is movably coupled to the distal mounting section. A pair of proximal actuators are coupled to the proximal mounting section, and a linkage system operably interconnects the actuators and the instrument guide assembly. The method further includes providing first control signals to one of the proximal actuators to cause the linkage system to move the instrument guide assembly in a first rotational degree of freedom. The method also includes providing second control signals to the other one of the proximal actuators to cause the linkage system to move the instrument guide assembly in a second rotational degree of freedom.

In another embodiment, a robotic surgical system comprises an instrument chassis assembly having a proximal mounting section and a distal mounting section. The chassis includes an instrument interface coupled to the proximal mounting section. The surgical system further comprises an actuation system coupled to the proximal mounting section. The surgical system further comprises a linkage system operably coupled between the actuation system and the distal mounting section. The linkage system includes an instrument guide. The surgical system further includes a surgical instrument configured to couple with the instrument interface and the instrument guide.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1 is a schematic depiction of a robotic surgical system according to an embodiment of the present disclosure.

FIGS. 2A, 2B, and 2C are a schematic depictions of a minimally invasive surgical system according to embodiments of the present disclosure.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Figure 1:
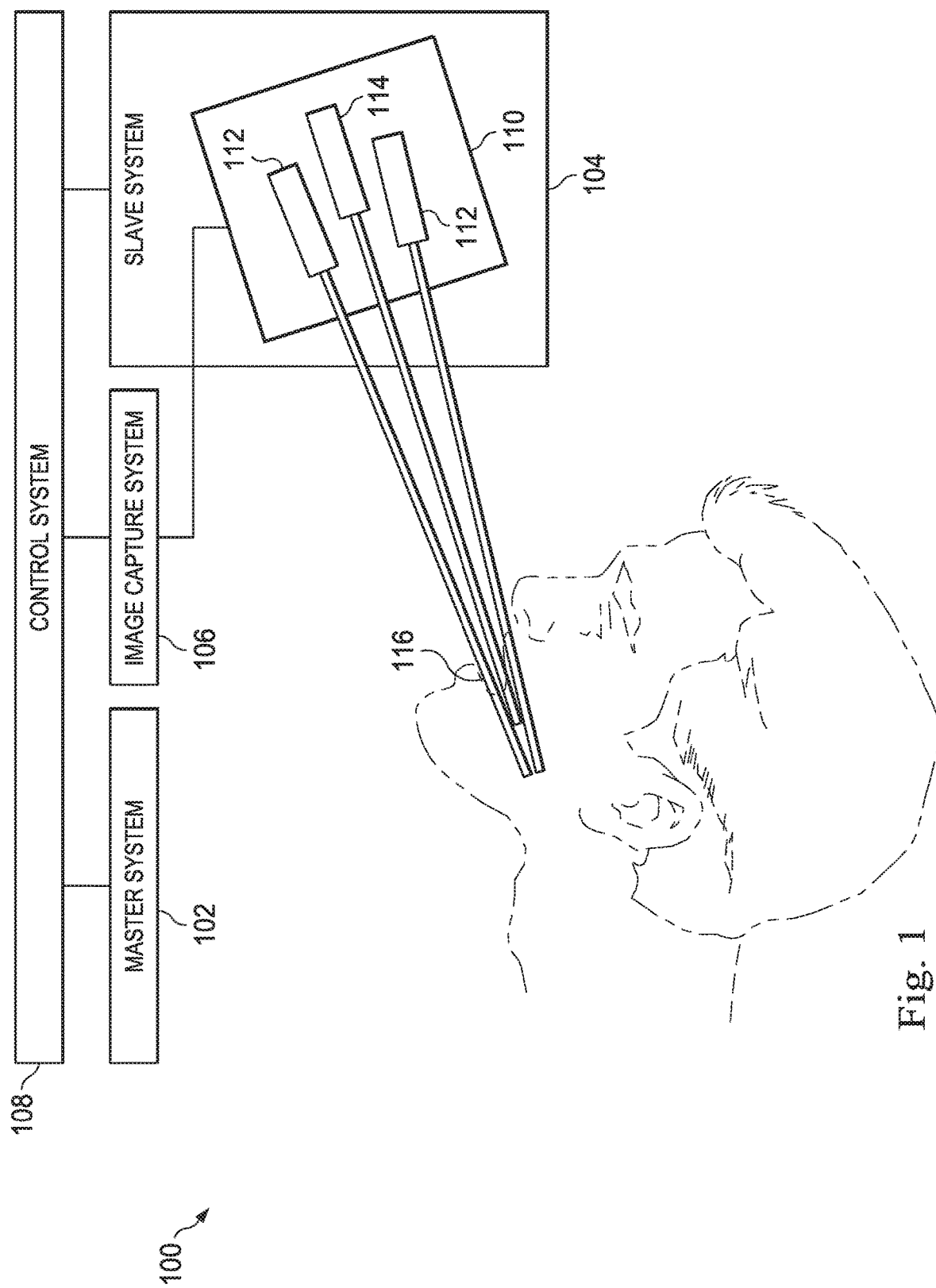

Referring to FIG. 1 of the drawings, a robotic surgical system is generally indicated by the reference numeral 100. The robotic surgical system 100 includes a master system 102, also referred to as a master or surgeon's console, for inputting a surgical procedure and a slave system 104, also referred to as a patient-side manipulator (PSM), for robotically moving surgical instruments at a surgical site within a patient. The robotic surgical system 100 is used to perform minimally invasive robotic surgery. One example of a robotic surgical system architecture that can be used to implement the systems and techniques described in this disclosure is a da Vinci® Surgical System manufactured by Intuitive Surgical, Inc. of Sunnyvale, Calif. Alternatively, a smaller scale robotic surgical system with a single manipulator arm may be suitable for some procedures. The robotic surgical system 100 also includes an image capture system 106, which includes an image capture device, such as an endoscope, and related image processing hardware and software. The robotic surgical system 100 also includes a control system 108 that is operatively linked to sensors, motors, actuators, and other components of the master system 102 and the slave system 104 and to the image capture system 106.

The system 100 is used by a system operator, generally a surgeon, who performs a minimally invasive surgical procedure on a patient. The system operator sees images, captured by the image capture system 106, presented for viewing at the master system 102. In response to the surgeon's input commands, the control system 108 effects servomechanical movement of surgical instruments coupled to the robotic slave system 104.

The control system 108 includes at least one processor and typically a plurality of processors for effecting control between the master system 102, the slave system 104, and the image capture system 106. The control system 108 also includes software programming instructions to implement some or all of the methods described herein. While control system 108 is shown as a single block in the simplified schematic of FIG. 1, the system may comprise a number of data processing circuits (e.g., on the master system 102 and/or on the slave system 104), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system 108 may support wireless communication protocols such as Bluetooth, IrDA, HomeRF, IEEE 802.11, DECT, and Wireless Telemetry.

The robotic surgical system 100 further includes an instrument chassis 110 that couples to the slave system 104. The instrument chassis 110 provides a common platform for coupling surgical instruments 112 and endoscope 114 for introduction into a patient entry point 116. In this embodiment, the patient entry point is a human mouth for providing access to the throat or larynx. It will be appreciated that the embodiments of this disclosure may be used for accessing body tissues through other natural or surgically created orifices.

Figure 2A:
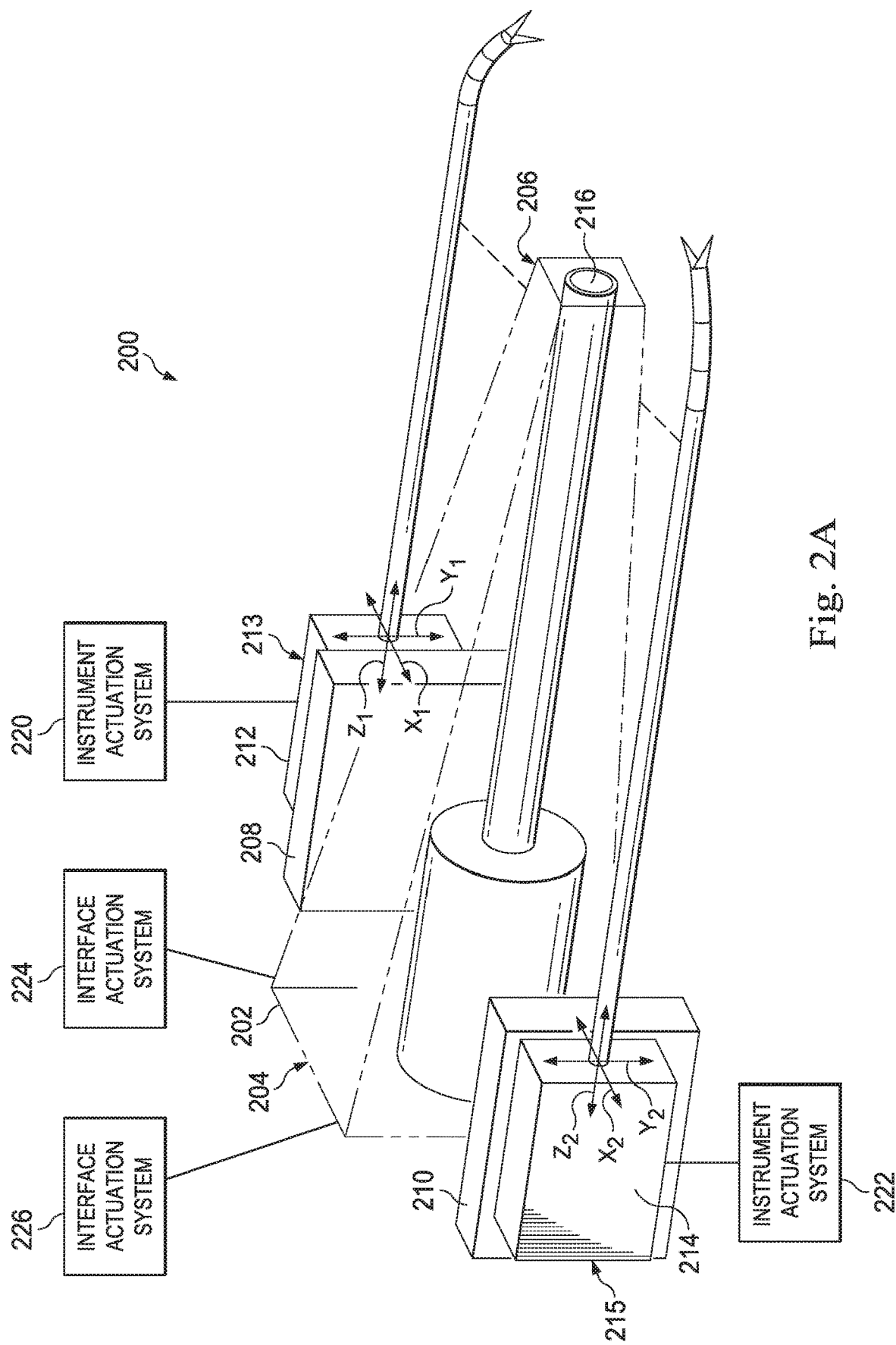

FIG. 2A is a schematic depiction of a minimally invasive surgical system 200 according to an embodiment of the present disclosure. The system 200 includes an instrument chassis 202 having a proximal section 204 and a distal section 206. The chassis 202 supports an endoscope 216. Generally, the dimensions and shape of the chassis at its distal section 206 are reduced compared to its proximal end 204 to minimize the volume of the surgical equipment near the surgical entry point. Instrument interfaces 208, 210 are movably mounted to the proximal section 204 of the instrument chassis 202. Surgical instrument 212 is mounted at its proximal end 213 to the instrument interface 208. Surgical instrument 214 is mounted at its proximal end 215 to the instrument interface 210. The interface 208 drives movable components in the surgical instrument 212 as described in U.S. Pat. No. 6,491,701 which is incorporated by reference herein, in its entirety. The interface 210 drives the instrument 214 in a similar way. The surgical instruments 212, 214 are also movably coupled to the distal section 206 of the chassis 202. As will be described in detail below, the instrument interfaces 208, 210 are mounted to the proximal section 204 of the chassis 202 such that rotational and linear motion is permitted. Specifically, an instrument interface mounting or a flexible instrument shaft permits a pitch motion of the instrument interfaces 208, 210 relative to the chassis 202, a yaw motion of the instrument interfaces relative to the chassis and an insertion sliding motion of the instrument interfaces relative to the chassis. The system 200 functions similar to the manner in which chopsticks operate, in that small motions at the proximal end of the tool, near a pivot location, can correspond to larger motions at the distal end of the tool for manipulating objects.

An actuation system 220 operates the components of instrument 212, such as an end effector and various wrist joints. An actuation system 222 operates the components of instrument 214, such as an end effector and various wrist joints. The actuation systems 220, 222 may include motors, actuators, drive systems, control systems, and other components for effecting the control of the instruments. An interface actuation system 224 controls the movement of the instrument 212 with respect to the chassis 202, and an interface actuation system 226 controls the movement of the instrument 214 with respect to the chassis 202. The reference system $X_1, Y_1, Z_1$ moves with the instrument 212 and the reference system $X_2$, $Y_2$, $Z_2$ moves with the instrument 214. Although the surgical system 200 may be configured to manipulate two instruments as shown, however in alternative embodiments, the system may be used to control the movement of more than two instruments.

Figure 2B:
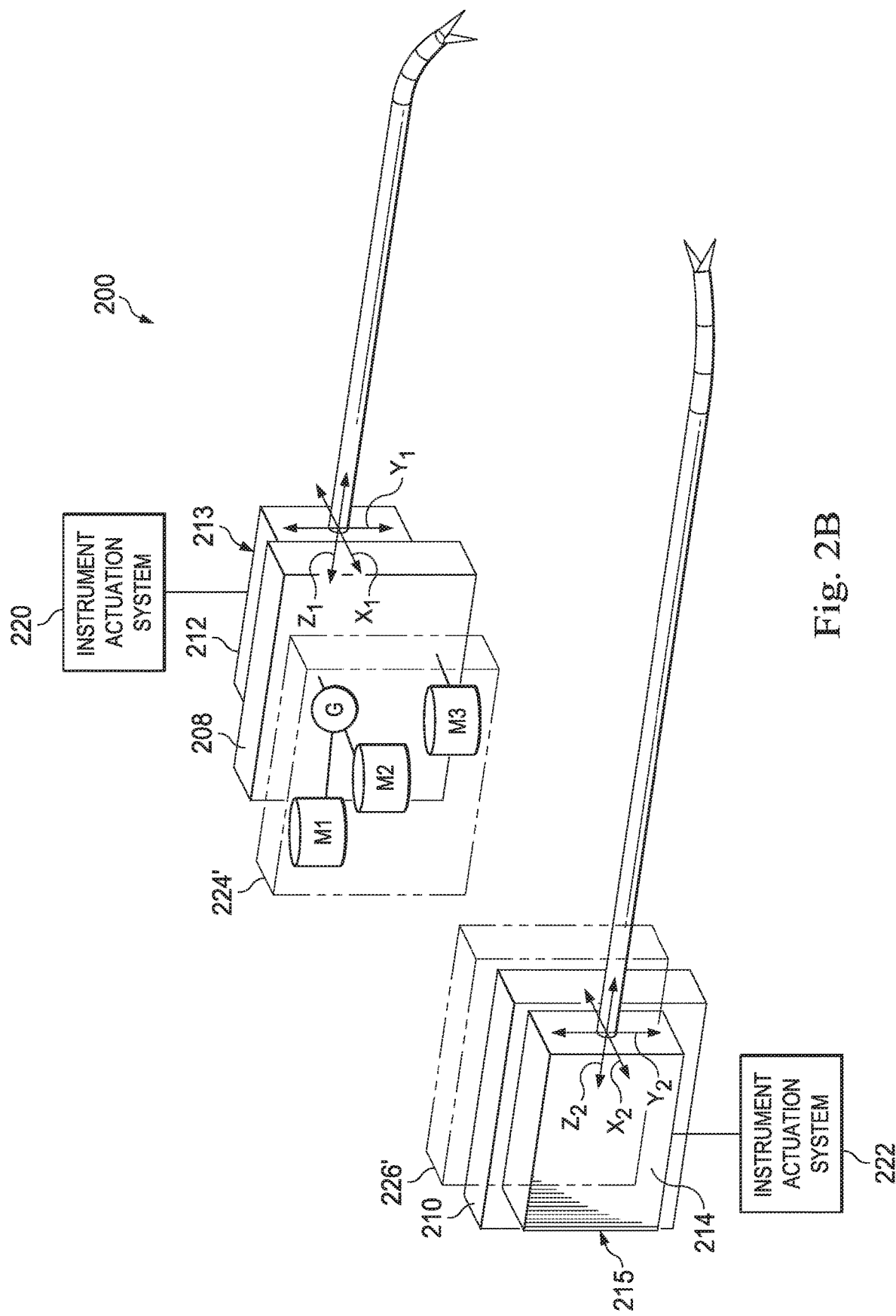
Figure 3:
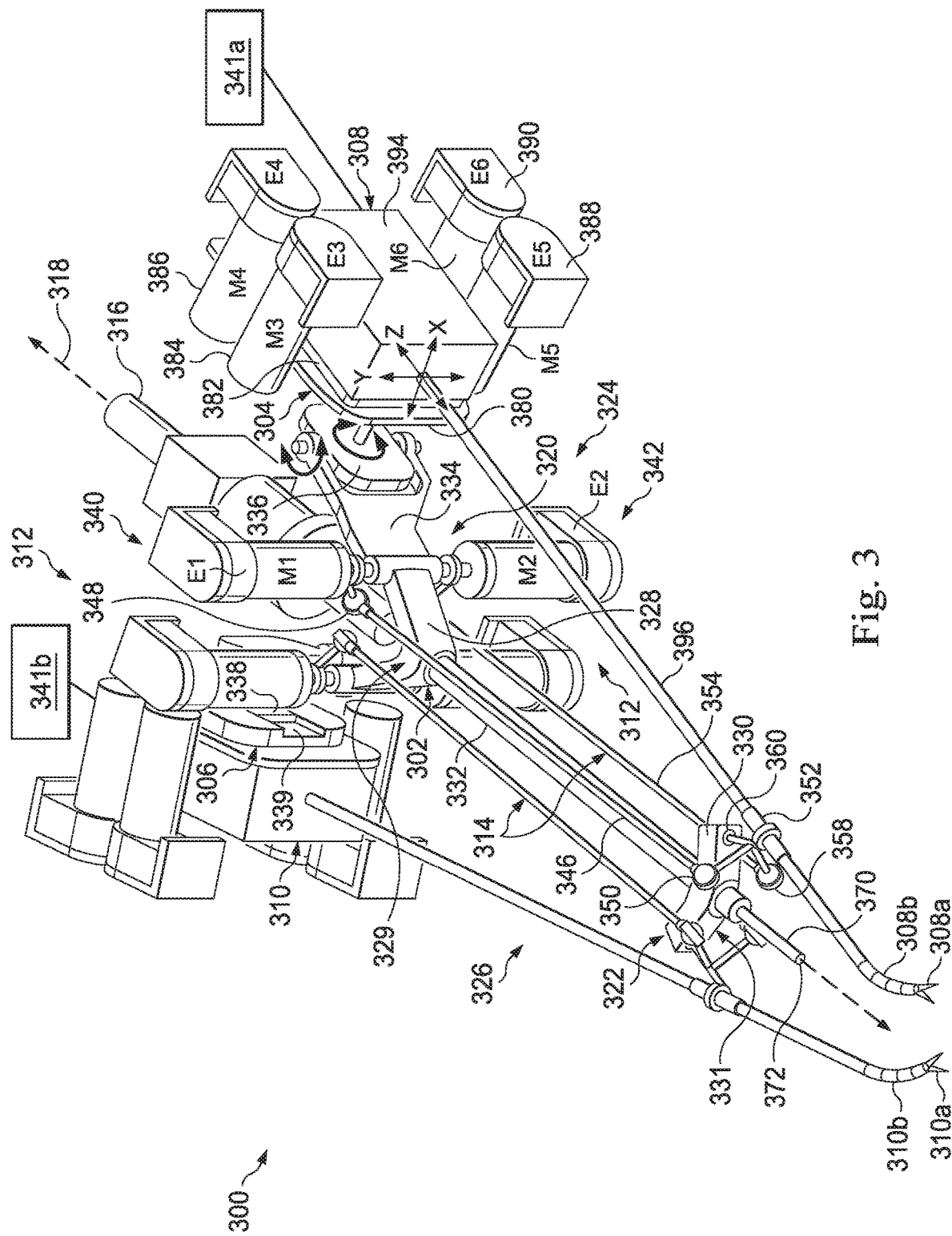
FIG. 3 is a perspective view of a minimally invasive surgical system according to another embodiment of the present disclosure.

FIG. 2B is a schematic depiction of the minimally invasive surgical system 200 according to another embodiment of the present disclosure. In this embodiment the interface actuation system 224' includes a motor M1 driving an orientation system G (e.g., a gimbal system such as shown in FIG. 3, gimbal components 334, 336) to control the proximal instrument interface 208 to move in a yaw movement (e.g., about the axis $Y_1$). The interface actuation system 224' also includes a motor M2 driving the orientation system G to control the proximal instrument interface 208 to move in a pitch movement (e.g., about the axis $X_1$). The interface actuation system 224' also includes a motor M3 to control the proximal instrument interface 208 to move axially along the axis $Z_1$ (e.g., for instrument insertion and withdrawal). Although not shown in detail, the interface actuation system 226' may include similar components for effecting similar motion in the proximal instrument interface 210. Thus, in this embodiment, the motion of the instruments may be controlled at the proximal end without support or control at the distal end. In this embodiment, the interface actuation systems 224' and 226' are between the proximal instrument interfaces 208, 210. Although the surgical system 200 may be configured to manipulate two instruments as shown, however in alternative embodiments, the system may be used to control the movement of more than two instruments.

Figure 2C:
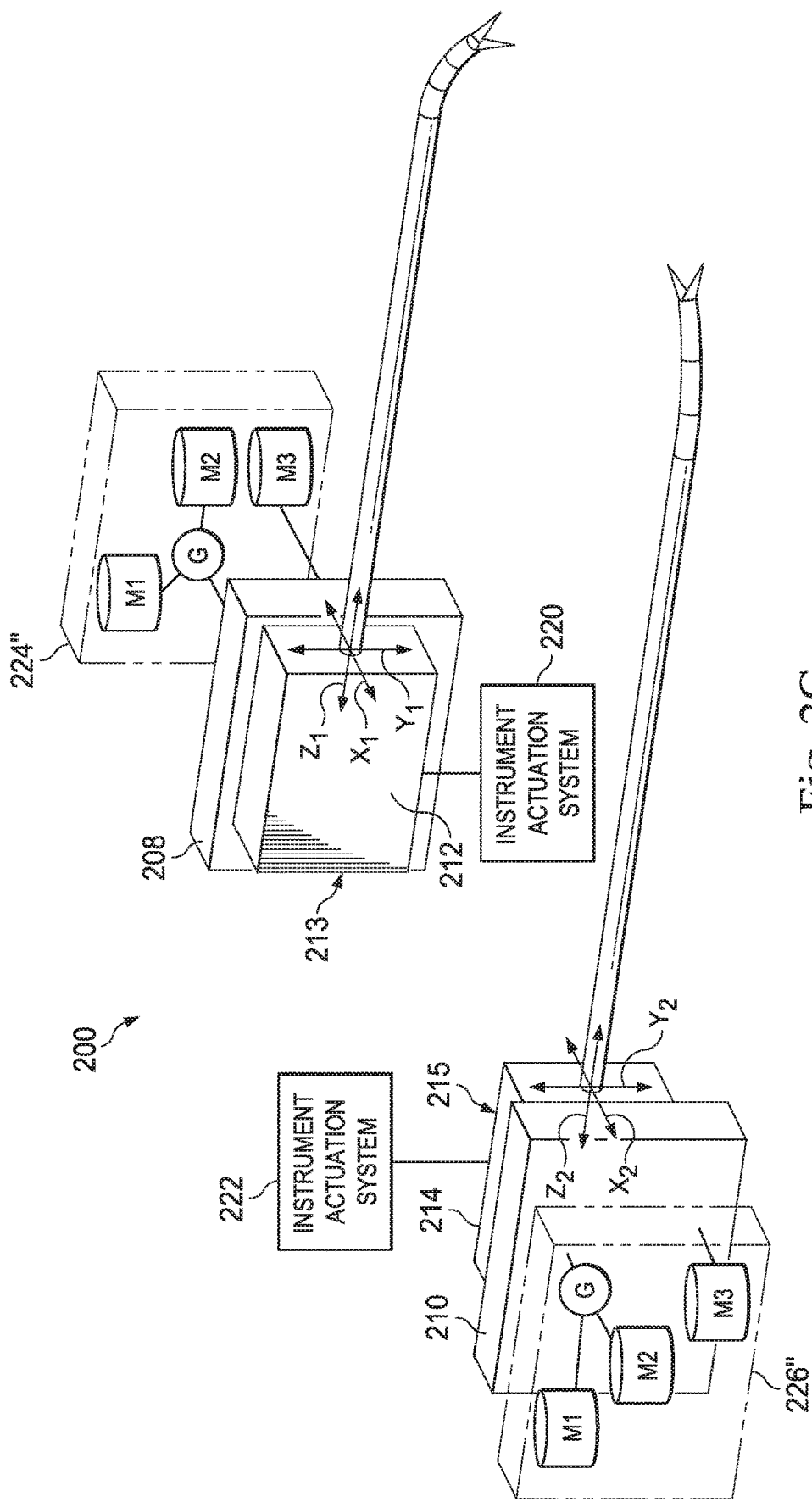

FIG. 2C is a schematic depiction of the minimally invasive surgical system 200 according to another embodiment of the present disclosure. In this embodiment, the interface actuation systems 224" and 226" are substantially similar to interface actuation systems 224' and 226', respectively, but in this embodiment, the proximal instrument interfaces 208, 210 are between the interface actuation systems 224" and 226". Although the surgical system 200 may be configured to manipulate two instruments as shown, however in alternative embodiments, the system may be used to control the movement of more than two instruments.

Earlier methods and systems of robotic surgery involved the use of a surgical instrument that was coupled to a robotic manipulator arm and to an insertion linkage system that constrained motion of the surgical instrument about a remote center of motion aligned along the shaft of the surgical instrument and coincident with a patient entry point, such as an entry incision. Further details of these methods and systems are described in U.S. Pat. Nos. 5,817,084 and 6,441,577, which are incorporated by reference herein in their entirety. The embodiments of this disclosure remove the constraint of the remote center of motion at the patient entry point and permit a surgical instrument to pivot, with at least one rotational degree of freedom, about a location in space near or coincident with a proximal end of the surgical instrument. The proximal pivot locations may be, for example, approximately 30 cm from the patient entry point when using a surgical instrument with an approximate 40-50 cm length.

FIG. 3 is a perspective view of a minimally invasive surgical system 300 according to another embodiment of the present disclosure. The system 300 may be effective to avoid instrument collisions when working in small spaces. The system 300 includes an instrument chassis 302 and instrument interfaces 304, 306 for mounting surgical instruments 308, 310, respectively to the chassis. The surgical instrument 308 includes an end effector 308a and a wrist mechanism 308b. The surgical instrument 310 includes an end effector 310a and a wrist mechanism 310b. The surgical instruments 308, 310 move independently of one another based upon control input signals originating from the master system 102 and manipulator actuation signals from control system 108. The system 300 further includes a chassis mounted actuator system 312 and a linkage system 314 interconnecting the actuator system 312 with the surgical instruments 308, 310. An image capture system 316 is supported by the chassis 302 and is generally aligned along a central axis 318 (in a Z-axis direction) through the chassis.

In greater detail, the instrument chassis 302 includes a proximal portion 320 and a distal portion 322. The system 300 generally includes a left lateral half 324 and a right lateral half 326 split generally about the central axis 318. In this embodiment, the structures and function of the right and left lateral halves of the system 300 are generally the same. Therefore, a full description of the structure and function of the system 300 will be directed toward the left lateral half 324 with the understanding that the structures and function of the right lateral half 326 are the same.

The instrument chassis 302 includes a bridge 328 located at a proximal end 329 of the chassis and includes a bridge 330 located at a distal end 331 of the chassis. A support tube 332 extends generally along the axis 318 and supports the image capture system 316. The support tube 332 rigidly connects the bridges 328, 330. The components of the instrument chassis may be formed of relatively rigid metals, plastics, or ceramics. The instrument chassis 302 further includes a gimbal support 334 pivotally connected to a gimbal plate 336. The gimbal system 334, 336 permits a yaw motion of the surgical instrument 308 (i.e., a rotational degree of freedom about a Y-direction axis) and permits a pitch motion of the surgical instrument 308 (i.e., a rotational degree of freedom about an X-direction axis. The motion of the gimbal system 334, 336 is passive, in that the motion is responsive to other actuated forces in the system 300 as will be described in greater detail. In alternative embodiments, other joint or pivot systems, including multi-axis gimbals, ball/socket joints, and hinges, may provide one or more degrees of freedom at the proximal section of the chassis.

The instrument chassis 302 also includes a guide (not shown) slidably engaged with a track (not shown) of the instrument interface 304. A guide 338 and track 340 are more clearly visible on the right half 326 of the system 300. The guide and track of the left half 324 permit insertion motion of the surgical instrument 308 generally along a Z-direction axis. Insertion drive systems 341a, 341b are coupled to the instruments 308, 310, respectively, to provide a driven insertion motion that moves the guide and track relative to one another. The insertion drive systems 341a, 341b include a drive motor and a drive mechanism such as a lead screw, ball screw, cable drive, or rack and pinion system. Alternatively, the motion of the guide/track may be passive, in that the motion is responsive to other actuated forces in the system 300.

The left half of the actuation system 312 includes actuators 340, 342 coupled to the chassis 302. The actuators 340, 342 each include a motor M1, M2, respectively with a drive mechanism that provides variable and controllable force and position control and an encoder E1, E2, respectively for providing the control system 108 with the rotational position of the respective motor drive shafts. Further details of the actuation system, including suitable alternatives, are provided in U.S. Pat. No. 5,792,135 which is incorporated by reference herein in its entirety. The actuators 340, 342 are coupled to the linkage system 314 which transmits the actuation. Each actuator provides a predetermined type of actuation. For example, the actuator 340 provides an actuated pitch motion (about an X-direction axis), and the actuator 342 provides an actuated yaw motion (about a Y-direction axis).

The left half of the linkage system 314 includes an actuation rod 346 coupled between ball and socket joints 348, 350. The ball and socket joint 348 is coupled to the actuator 340. The linkage system 314 also includes an instrument guide 352 coupled to ball and socket joint 350. In this embodiment, the instrument guide 352 is a tubular sleeve sized to receive the shaft of the surgical instrument 308. In alternative embodiments, the instrument guide may be a ring, a tray, an opening tube, or other structure to movably link the surgical instrument to the chassis. The linkages 346, 348, 350 serve to transmit a motion from the actuator 340 to the instrument guide 352. Specifically, the linkages may move the instrument guide 352 in a generally linear Y-direction or in a rotational pitch motion. The linkage system 314 also includes an actuation rod 354 coupled between ball and socket joints 356 (view obstructed by chassis), 358. The ball and socket joint 350 is coupled to the actuator 342. The instrument guide 352 is also coupled to the ball and socket joint 358. The linkages 354, 356, 358 serve to transmit a motion from the actuator 342 to the instrument guide 352. Specifically, the linkages may move the instrument guide 352 in a generally X-direction or in a rotational yaw motion. The linkage system 314 further includes a ball joint 360 positioned within a socket formed in the distal bridge 330. The ball joint 360 is coupled to the instrument guide 352 to tether the instrument guide to the chassis 302. The components of the linkage system may be formed of relatively rigid metals, plastics, or ceramics. The components of the linkage system may be sterilizable or disposable. The components of the linkage system may have a small cross-sectional area to minimize the volume of the surgical equipment near the patient entry point. For example, the rod linkages may have a diameter of approximately 1-3 mm. In alternative embodiments, other linkage components may be suitable to transmit a predetermined motion. Such alternative components may include unidirectional hinge joints, saddle joints, slide joints, flexible components such as springs, and fixed joints.

The chassis 302 also supports the image capture system 316. More specifically, an endoscopic instrument 370 of the image capture system 316 extends through the support tube 332. The endoscopic instrument 370 has a viewing end 372 and is operatively connected to a viewer in the master system 102 to display an image captured at the viewing end to the surgeon or other viewer. The endoscopic instrument 370 may be fixed relative to the instrument chassis 302 or may be constrained to movement along an insertion axis generally aligned with the axis 318. Alternatively, the endoscopic instrument may be steerable, pivotable, or otherwise articulatable relative to the instrument chassis to change the viewpoint of the viewing end.

Figure 4:
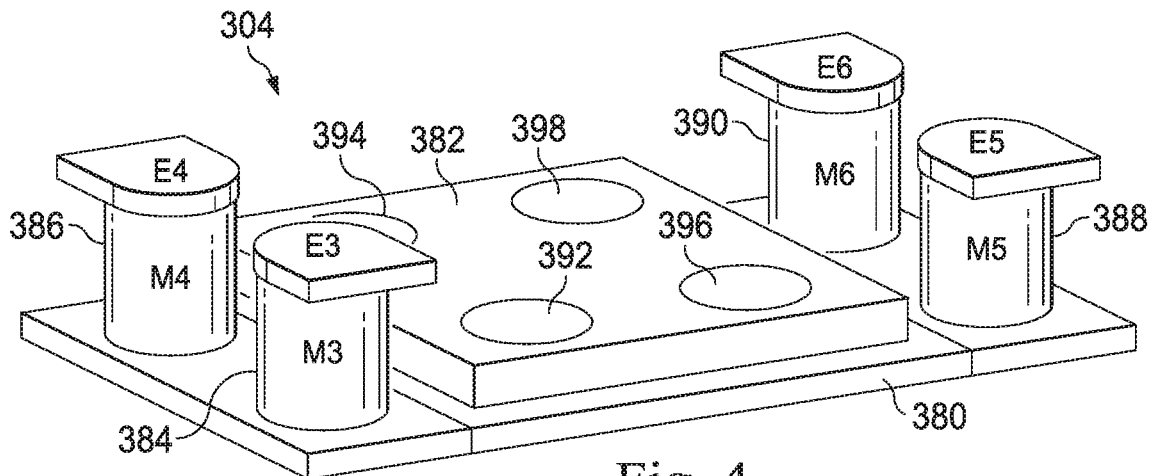
FIG. 4 is a schematic depiction of an instrument interface of a robotic surgical system according to an embodiment of the present disclosure.

The instrument interface 304 is shown in greater detail in FIG. 4. A chassis interface plate 380 (which may be considered part of the chassis or part of the interface) is rotatably connected to an instrument interface plate 382. The rotational motion may be provided by a swivel joint, a ball/socket joint, or other known mechanism to provide full or partial rotational motion. The rotational motion between the plates 380, 382 is passive, in that the motion is responsive to other actuated forces in the system 300 as will be described in greater detail.

Actuators 384, 386, 388, 390 are operably coupled to interface discs 392, 394, 396, 398, respectively. A more detailed description of the interface discs and their function in driving a predetermined motion in an attached surgical instrument is fully described, for example, in U.S. Pat. No. 7,963,913, filed Dec. 10, 2006, disclosing "Instrument Interface of Robotic Surgical System," which is incorporated by reference herein in its entirety. In this embodiment, each actuator includes a motor M and an encoder E. Each actuator 384-390 influences a specific motion in the end effector 308*a* and/or the wrist mechanism 308*b* of the surgical instrument 308. As one example, the actuator 384 may control a roll motion of the wrist mechanism 308*b*. The actuator 386 may control an actuated pitch motion of the wrist mechanism 308*b*. The actuator 388 and the actuator 390 may be coordinated to control actuated yaw and grip motions of the wrist mechanism. The assigned controls for the various actuators are merely examples. In alternative embodiments, the actuators may be configured to control different motions in the surgical end effector or wrist. For example a single actuator may control grip while the coordinated combination of two actuators may control pitch and yaw of the wrist mechanism.

As shown in FIG. 3, the surgical instrument 308 includes a proximal housing 394 that couples to the interface 304. An instrument shaft 396 extends between the proximal housing 394 and the wrist mechanism 308*b*. Various embodiments of surgical instruments, end effectors, and wrist mechanisms are explained in detail in U.S. Pat. Nos. 5,792,135; 6,331,181; and 6,817,974, which are incorporated by reference herein in their entirety.

As assembled, the proximal housing 394 is coupled to the instrument interface 304 and the shaft 396 is inserted through the instrument guide 352. The shaft 396 passively slides within the instrument guide 352, in response to actuated forces in the system 300. For example, actuators 340, 342 may provide coupled motion for pitch about axis X and for yaw about axis Y. When the actuators 340, 342 both move in the same direction about the axis Y, the shaft 396 moves in yaw. When the actuators 340, 342 move in different directions about the axis Y, the shaft 396 moves in pitch. The combined movement of the actuators 340, 342 may be governed by a 2×2 coupling matrix to move the shaft 396 in a range of directions.

The system 300 as described, allows surgical access to body tissues through small natural or surgically created patient entry points. The system may be particularly suited for surgically accessing larynx or throat tissues via an open patient mouth or for accessing uterine tissues via the cervix to perform a vaginal hysterectomy. Alternatively, the system 300 may be used to perform surgery that may be tiring for a surgeon or require awkward positioning, such as breast surgery. As compared to robotic surgical systems that require multiple large, dedicated manipulator arms to control rotational and insertion motions of the surgical instruments, the system 300 uses a minimized-size chassis that supports multiple surgical instruments. Although system 300 describes the use of two surgical instruments coupled to a common chassis, in alternative embodiments, three or more surgical instruments may be mounted and controlled from a common chassis. Locating the actuation system for controlling the movement of the instrument guides at a proximal section of the chassis minimizes the number and size of the structures needed at intermediate or distal locations along the instrument shaft to support and control multiple surgical instruments. The linkage system allows the actuation system to remotely control the motion of the instrument guides.

Prior to the use of the system 300, a manipulator arm of the slave manipulator system 104 is positioned and locked into place. The manipulator arm may be, for example, an arm of a da Vinci® Surgical System or may be a smaller scale manipulator with a linked arm having up to six degrees of freedom. In some embodiments, the manipulator arm supporting the system 300 is not controlled by motors. It may be a passive lockable arm with one or more balanced joints having brakes or locks. A passive lockable arm may move freely in a released configuration, allowing the system to be positioned at the surgical site in a selected orientation. The passive lockable arm is then moved to a locked configuration with brakes holding the selected orientation. In other embodiments, the system 300 may be held by an iron intern, a passive multi-jointed unbalanced arm that may be manually locked.

Figure 5:
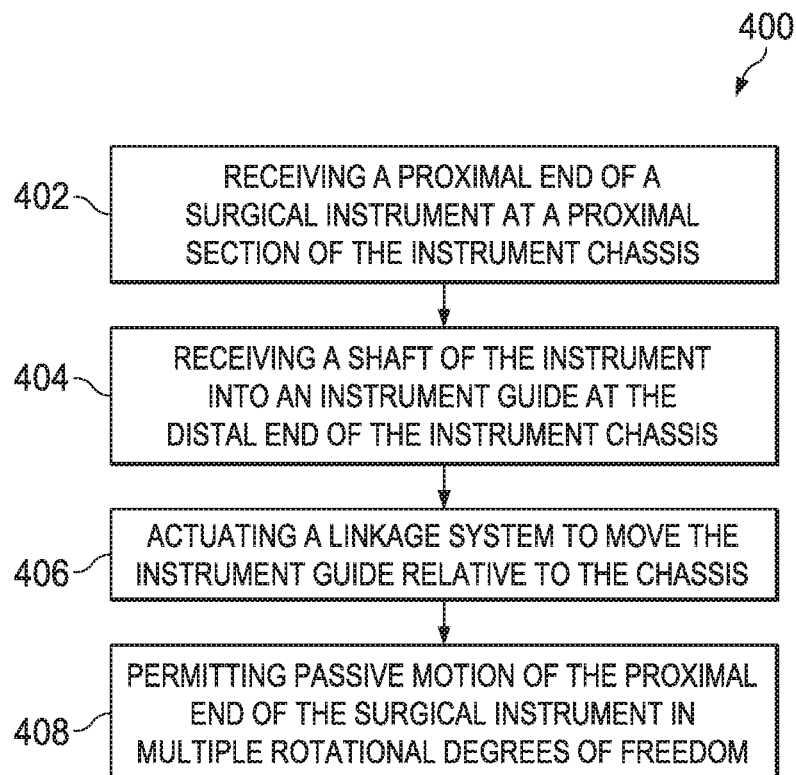
FIG. 5 is a method of robotic surgery according to an embodiment of the present disclosure.

Referring now to FIG. 5, a general method 400 of robotic surgery using the system 300 is provided. At 402, the housing 394 at the proximal end of the surgical instrument 308 is received into engagement with the instrument interface 304. At 404, the shaft 396 of the surgical instrument 309 is received into the instrument guide 352 at the distal end of the instrument chassis 302. More specifically, a distal or intermediate portion of the shaft 396 is received into the instrument guide 352. At 406, the actuation system 312 actuates linkage system 314 to move the instrument guide 352 relative to the instrument chassis 302. More specifically, the actuator 340 receives control signals from the control system 108 to drive the linkage system 314, including moving the ball and socket joint 348 which moves the rod 346. Further, the actuator 342 receives control signals from the control system 108 to drive the linkage system 314, including moving the ball and socket joint 356 which moves the rod 354. When rod 346 and rod 354 move together, instrument guide 352 moves along an X-direction axis. When rod 346 and rod 354 move oppositely, instrument guide 352 moves along a Y-direction axis. If only one rod 346 or 354 is moving, instrument guide 352 moves at an angle to both the X and Y-direction axes. The instrument guide 352 is tethered to the distal portion 330 of the chassis 302 by the ball joint 360.

At 408, in response to the motor-driven actuation of the instrument guide 352, the proximal end of the surgical instrument 308 is permitted to passively move in multiple rotational degrees of freedom. More specifically, the proximal end of the surgical instrument 308 is permitted to passively rotate (yaw) with the gimbal plate 336 about a Y-direction axis. Additionally, the proximal end of the surgical instrument 308 is permitted to passively rotate (pitch) with the instrument interface plate 382 relative to the chassis interface plate 380 about an X-direction axis. Because of the proximal location of the passive rotational joints, the movement of the instrument guide 352 near a distal or intermediate location of the instrument shaft 396 affects a smaller scale motion at the proximal end of the surgical instrument 308. The smaller scale motion at the proximal end of the surgical instruments reduces or prevents proximal end instrument collisions. To avoid robotic arm collisions, some existing systems may require spacing between instrument anatomic entry points of approximately 8-9 cm. The systems of this disclosure may allow closer instrument spacing while avoiding robotic arm collisions.

In an alternative embodiment, one or more of the gimbals or other rotational joints at the proximal end of the chassis may be replaced with fixed joints. In this embodiment, a flexible instrument shaft may be used, allowing the surgical instrument a limited amount of rotational movement relative to the chassis.

Figure 6:
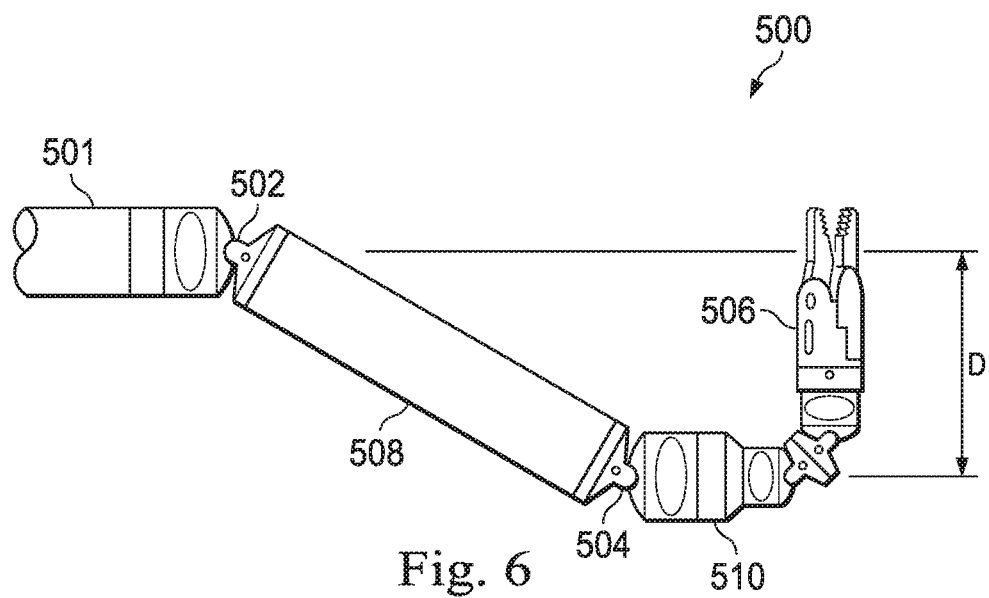
FIG. 6 is a side view a distal end of a surgical instrument according to an embodiment of the present disclosure.

To provide additional degrees of freedom to the surgical instrument and to increase the workspace between to relatively parallel instruments inserted into a narrow patient entry point, a parallel motion mechanism or "joggle joint" may be added to the distal end of the surgical instrument. The parallel motion mechanism includes a series of joints and linkages at the distal of the surgical instrument, proximal of the end effector, that permit lateral displacement of the end effector. A description of joggle joints and parallel motion mechanisms is provided in U.S. Pat. No. 7,942,868 and U.S. patent application Ser. No. 12/489,566 which are incorporated by reference herein in their entirety. FIG. 6 is a side view of a distal surgical instrument section 500 with a shaft 501. The section 500 includes a joint 502, a joint 504, a joint 506, and linkages 508, 510. The joints 502, 504 permit +/−45° of rotation and the joint 510 permits +/−90° of rotation. The joints 502, 504, 506 and linkages 508, 510 provide a lateral displacement D from the axis of the shaft 510, allowing for a greater surgical workspace between generally parallel surgical instruments.

One or more elements in embodiments of the invention may be implemented in software to execute on a processor of a computer system such as control system 108. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An instrument chassis for a robotic surgical system, the instrument chassis comprising:

a bridge member;

a first instrument guide member configured to receive a first surgical instrument;

a second instrument guide member configured to receive a second surgical instrument, wherein each of the first instrument guide member and the second instrument guide member is moveably coupled to the bridge member such that each of the first instrument guide member and the second instrument guide member is moveable in at least one degree of freedom relative to the bridge member; and a central instrument guide member coupled to the bridge member between the first instrument guide member and the second instrument guide member, the central instrument guide member being configured to receive a third surgical instrument, wherein each of the first instrument guide member and the second instrument guide member is slidably movable relative to the bridge member.

2. The instrument chassis of claim 1, wherein each of the first instrument guide member and the second instrument guide member is pivotably moveable relative to the bridge member.

3. The instrument chassis of claim 1, wherein the bridge member is rigidly coupled to a proximal chassis by a support section extending between the bridge member and the proximal chassis.

4. The instrument chassis of claim 1, wherein the third surgical instrument is an image capture device.

5. The instrument chassis of claim 1, wherein the third surgical instrument extends through the central instrument guide member along a central chassis axis.

6. The instrument chassis of claim 1, wherein the third surgical instrument is slidably moveable relative to the central instrument guide member.

7. The instrument chassis of claim 1, wherein the central instrument guide member is moveable in at least one degree of freedom relative to the bridge member.

8. The instrument chassis of claim 1, wherein the instrument chassis is located proximal to a patient entry site.

9. A surgical system comprising:
   an arm of a manipulator system;
   an instrument chassis including a bridge member;
   a first surgical instrument including a proximal portion and a distal portion; and
   a first instrument guide member coupled to the bridge member and moveable relative to the bridge member in at least one degree of freedom, wherein the first instrument guide member is adapted to receive the distal portion of the first surgical instrument, and wherein the arm is configured to interface with the proximal portion of the first surgical instrument to move the first surgical instrument relative to the bridge member in the at least one degree of freedom,
   wherein the first instrument guide member is pivotably movable relative to the bridge member.

10. The surgical system of claim 9, wherein the first instrument guide member is slidably movable relative to the bridge member.

11. The surgical system of claim 9, wherein the bridge member is rigidly coupled to a proximal chassis by a support section extending between the bridge member and the proximal chassis.

12. The surgical system of claim 9, wherein the distal portion of the first surgical instrument is slidably movable relative to the first instrument guide member.

13. The surgical system of claim 9, further comprising a central instrument guide member coupled to the bridge member, the central instrument guide member configured to receive a third surgical instrument, wherein the third surgical instrument is an image capture device.

14. The surgical system of claim 13, wherein the third surgical instrument extends through the central instrument guide member along a central chassis axis.

15. The surgical system of claim 14, wherein the third surgical instrument is slidably moveable relative to the central instrument guide member.

16. The surgical system of claim 13, wherein the central instrument guide member is moveable in at least one degree of freedom relative to the bridge member.

17. The surgical system of claim 9, wherein the bridge member is positioned proximal to a patient entry site.

18. A robotic surgical system comprising:
    a bridge member;
    a surgical instrument including a shaft, the surgical instrument defining a central instrument axis; and
    an instrument guide member coupled to the bridge member, the instrument guide member configured to receive the shaft of the surgical instrument and to moveably couple the surgical instrument to the bridge member such that the central instrument axis is moveable in at least one degree of freedom relative to the bridge member,
    wherein the shaft of the surgical instrument is slidably moveable relative to the instrument guide member.

19. The robotic surgical system of claim 18, wherein the instrument guide member is at least one of slidably moveable relative to the bridge member or pivotably moveable relative to the bridge member.

20. The robotic surgical system of claim 18, wherein the bridge member is located proximal to a patient entry site.

* * * * *